(12) United States Patent
 Varnedoe et al.

(10) Patent No.: US 9,240,253 B2
(45) Date of Patent: Jan. 19, 2016

(54) COLUMN GEOMETRY TO MAXIMIZE ELUTION EFFICIENCIES FOR MOLYBDENUM-99

(75) Inventors: Jennifer Varnedoe, Leland, NC (US); William Earl Russell, II, Wilmington, NC (US); Bradley D. Bloomquist, Wilmington, NC (US); Melissa Allen, Wilmington, NC (US); James Edward Paine, Wilmington, NC (US); Alan Anthony Alvarez, High Point, NC (US)

(73) Assignee: GE-HITACHI NUCLEAR ENERGY AMERICAS LLC, Wilmington, NC (US)

( * ) Notice: Subject to any disclaimer, the term of this patent is extended or adjusted under 35 U.S.C. 154(b) by 0 days.

(21) Appl. No.: 12/755,714

(22) Filed: Apr. 7, 2010

(65) Prior Publication Data
US 2011/0250107 A1  Oct. 13, 2011

(51) Int. Cl.
*A61K 51/02* (2006.01)
*B01D 15/14* (2006.01)
(Continued)

(52) U.S. Cl.
CPC ............ *G21G 1/0005* (2013.01); *A61K 51/025* (2013.01); *B01D 15/14* (2013.01); *B01D 15/18* (2013.01); *B01D 15/22* (2013.01);
(Continued)

(58) Field of Classification Search
CPC ........ B01D 15/08; B01D 15/14; B01D 15/18; B01D 15/22; B01D 15/10; C22B 34/12; C22B 34/34; G01N 30/60; G01N 30/6052; G01N 30/6065; A61K 51/00; A61K 51/02; A61K 51/0205

USPC ............. 210/198.2, 511, 634, 656, 459, 460; 73/61.52, 61.53; 422/70, 159, 256, 422/257; 423/6, 8, 249; 424/1.11, 1.61
See application file for complete search history.

(56) References Cited

U.S. PATENT DOCUMENTS 2,487,574 A * 11/1949 Meng ............................ 210/656
2,988,429 A *  6/1961 Cooley .......................... 422/257
(Continued)

FOREIGN PATENT DOCUMENTS

CN          1450349 A     10/2003
CN         201195740 Y     2/2009
(Continued)

OTHER PUBLICATIONS

Search Report issued in connection with EP Application No. 09165248.7, Jun. 5, 2012.
(Continued)

*Primary Examiner* — Joseph Drodge
(74) *Attorney, Agent, or Firm* — Harness, Dickey & Pierce, P.L.C.

(57) ABSTRACT

At least one system for eluting a radioactive material and a method of eluting a radioactive material is provided. The system for eluting a radioactive material may include an elution column configured to enclose an radioactive material, a first sealing member sealing a first end of the elution column, a second sealing member sealing a second end of the elution column, an elution supply source connected to the first end of the elution column via a first needle, a collection system connected to the second end of the elution column via a second needle, and a filter in the elution column, the filter being configured to support the radioactive material and prevent the radioactive material from contacting the second needle.

24 Claims, 12 Drawing Sheets

(51) Int. Cl.
*B01D 15/18* (2006.01)
*B01D 15/22* (2006.01)
*C22B 34/12* (2006.01)
*C22B 34/34* (2006.01)
*G01N 30/60* (2006.01)
*G21G 1/00* (2006.01)

(52) U.S. Cl.
CPC ............... *C22B 34/12* (2013.01); *C22B 34/34* (2013.01); *G01N 30/6052* (2013.01); *G01N 30/6065* (2013.01); *G21G 2001/0042* (2013.01)

(56) References Cited

U.S. PATENT DOCUMENTS

| | | | |
|---|---|---|---|
| 3,250,058 A * | 5/1966 | Baddour | 95/85 |
| 3,462,245 A * | 8/1969 | Vernejoul et al. | 250/432 PD |
| 3,535,085 A * | 10/1970 | Shumate | 250/432 PD |
| 3,561,932 A * | 2/1971 | Gruverman et al. | 423/132 |
| 3,657,541 A * | 4/1972 | Deutsch et al. | 250/252.1 |
| 3,799,883 A * | 3/1974 | Arino et al. | 252/645 |
| 3,820,660 A * | 6/1974 | Halasz et al. | 210/198.2 |
| 3,902,849 A | 9/1975 | Barak et al. | |
| 3,970,583 A * | 7/1976 | Panek-Finda | 422/159 |
| 4,188,539 A | 2/1980 | Strecker | |
| 4,206,358 A | 6/1980 | Matthews | |
| 4,239,970 A | 12/1980 | Eckhardt et al. | |
| 4,280,053 A * | 7/1981 | Evans et al. | 250/432 PD |
| 4,387,303 A | 6/1983 | Benjamins | |
| 4,472,299 A | 9/1984 | Weisner | |
| 4,709,729 A | 12/1987 | Harrison | |
| 4,719,011 A * | 1/1988 | Shalon et al. | 210/198.2 |
| 4,738,834 A * | 4/1988 | Moore et al. | 423/2 |
| 4,782,231 A * | 11/1988 | Svoboda et al. | 423/249 |
| 4,879,431 A * | 11/1989 | Bertoncini | 435/308.1 |
| 5,206,346 A | 4/1993 | Taylor | |
| 5,275,789 A * | 1/1994 | Taylor | 422/159 |
| 5,340,476 A | 8/1994 | Berger et al. | |
| 5,564,104 A * | 10/1996 | Pourfarzaneh | 588/20 |
| 5,839,192 A | 11/1998 | Weems et al. | |
| 6,136,197 A | 10/2000 | Egorov et al. | |
| 6,153,252 A * | 11/2000 | Hossainy et al. | 427/2.3 |
| 6,157,036 A * | 12/2000 | Whiting et al. | 250/432 PD |
| 6,172,207 B1 * | 1/2001 | Damhaut et al. | 536/18.4 |
| 6,190,637 B1 | 2/2001 | Ino | |
| 6,375,230 B1 | 4/2002 | Jensen et al. | |
| 8,699,651 B2 * | 4/2014 | Bloomquist et al. | 376/202 |
| 2007/0189434 A1 | 8/2007 | Jensen et al. | |
| 2008/0200863 A1 | 8/2008 | Chomas et al. | |
| 2008/0237502 A1 | 10/2008 | Fago | |
| 2011/0206606 A1 * | 8/2011 | Chen et al. | 424/1.69 |

FOREIGN PATENT DOCUMENTS

| | | |
|---|---|---|
| EP | 1 241 680 A1 | 9/2002 |
| JP | 49-028319 B1 | 7/1974 |
| JP | 54101094 A | 8/1979 |
| JP | 04-343070 A | 11/1992 |
| JP | 05169544 A | 7/1993 |
| JP | 0829598 A | 2/1996 |
| JP | 2002516167 A | 6/2002 |
| JP | 2009503514 A | 1/2009 |
| JP | 2010-532219 A | 10/2010 |
| JP | 2010532219 A | 10/2010 |
| WO | WO-2009/006008 A1 | 1/2009 |

OTHER PUBLICATIONS

Office Action from corresponding EP Application No. 11161361.8, dated Feb. 20, 2013.

Unofficial English Translation of Chinese Office Action and Search Report issued in connection with corresponding CN Application No. 201110095591.1 on Sep. 12, 2014.

Unofficial English translation of Japanese Office Action issued in connection with corresponding JP Application No. 2011-065318 on Jan. 6, 2015.

\* cited by examiner

COLUMN GEOMETRY TO MAXIMIZE ELUTION EFFICIENCIES FOR MOLYBDENUM-99

BACKGROUND

1. Field

The invention relates to elution columns used for extracting technetium ions from radioactive titanium molybdate.

2. Description of the Related Art

Technetium-99m (m is metastable) is a radionuclide used in nuclear medical diagnostic imaging. Technetium-99m is injected into a patient which, when used with certain equipment, is used to image the patient's internal organs. However, technetium-99m has a halflife of only six (6) hours, therefore, readily available sources of technetium-99m are desired.

A method for obtaining technetium-99m uses a minimum of a two-step process. First, titanium molybdate is placed in a capsule, which is then irradiated in a nuclear reactor. Molybdenum-98 within the titanium molybdate absorbs a neutron during the irradiation process and becomes molybdenum-99 (Mo-99). Alternatively, molybdenum metal can be irradiated and titanium molybdate fainted after irradiation. Mo-99 is unstable and decays with a 66-hour half-life to technetium-99m. After the irradiation step, the radioactive titanium molybdate is removed from the capsule and placed in a column for elution. Subsequently, saline is passed through the radioactive titanium molybdate to remove the technetium-99m ions from the radioactive titanium molybdate.

SUMMARY

Example embodiments relate to at least one system for eluting a radioactive material and a method of eluting a radioactive material.

In accordance with an example embodiment, a system for eluting a radioactive material may include an elution column configured to enclose a radioactive material, a first sealing member sealing a first end of the elution column, a second sealing member sealing a second end of the elution column, an elution supply source connected to the first end of the elution column via a first needle, a collection system connected to the second end of the elution column via a second needle, and a filter in the elution column, the filter being configured to support the radioactive material and prevent the radioactive material from contacting the second needle.

In accordance with an example embodiment, a method for eluting a radioactive material may include mixing the radioactive material with an elution solution to form a mixture in a first cylinder, heating the mixture to form a gas including an ion, condensing the gas with the ion in a coiled portion of a tube to form a condensate that includes the ion, and collecting the condensate in a second cylinder.

In accordance with an example embodiment, a system for eluting a radioactive material may include a membrane enclosing and supporting the radioactive material, a spherical shaped capsule enclosing the membrane, an elution solution supply source configured to provide elution solution inside the spherical shaped capsule, and a collection system configured to receive eluant from the membrane.

BRIEF DESCRIPTION OF THE DRAWINGS

Example embodiments of the present invention will be more clearly understood from the following detailed description taken in conjunction with the accompanying drawings.

DETAILED DESCRIPTION OF THE EXAMPLE EMBODIMENTS

Example embodiments of the invention will now be described more fully with reference to the accompanying drawings, in which example embodiments are shown. The invention may, however, be embodied in different forms and should not be construed as limited to the embodiments set forth herein. Rather, these embodiments are provided so that this disclosure will be thorough and complete, and will fully convey the scope of the invention to those skilled in the art. In the drawings, the sizes of components may be exaggerated for clarity.

It will be understood that when an element or layer is referred to as being "on", "connected to", or "coupled to" another element or layer, it can be directly on, connected to, or coupled to the other element or layer or intervening elements or layers that may be present. In contrast, when an element is referred to as being "directly on", "directly connected to", or "directly coupled to" another element or layer, there are no intervening elements or layers present. As used herein, the term "and/or" includes any and all combinations of one or more of the associated listed items.

It will be understood that, although the terms first, second, etc. may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. Thus, a first element, component, region, layer, or section discussed below could be termed a second element, component, region, layer, or section without departing from the teachings of example embodiments.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

Embodiments described herein will refer to plan views and/or cross-sectional views by way of ideal schematic views. Accordingly, the views may be modified depending on manufacturing technologies and/or tolerances. Therefore, example embodiments are not limited to those shown in the views, but include modifications in configuration formed on the basis of manufacturing processes. Therefore, regions exemplified in figures have schematic properties and shapes of regions shown in figures exemplify specific shapes or regions of elements, and do not limit example embodiments.

Figure 1:
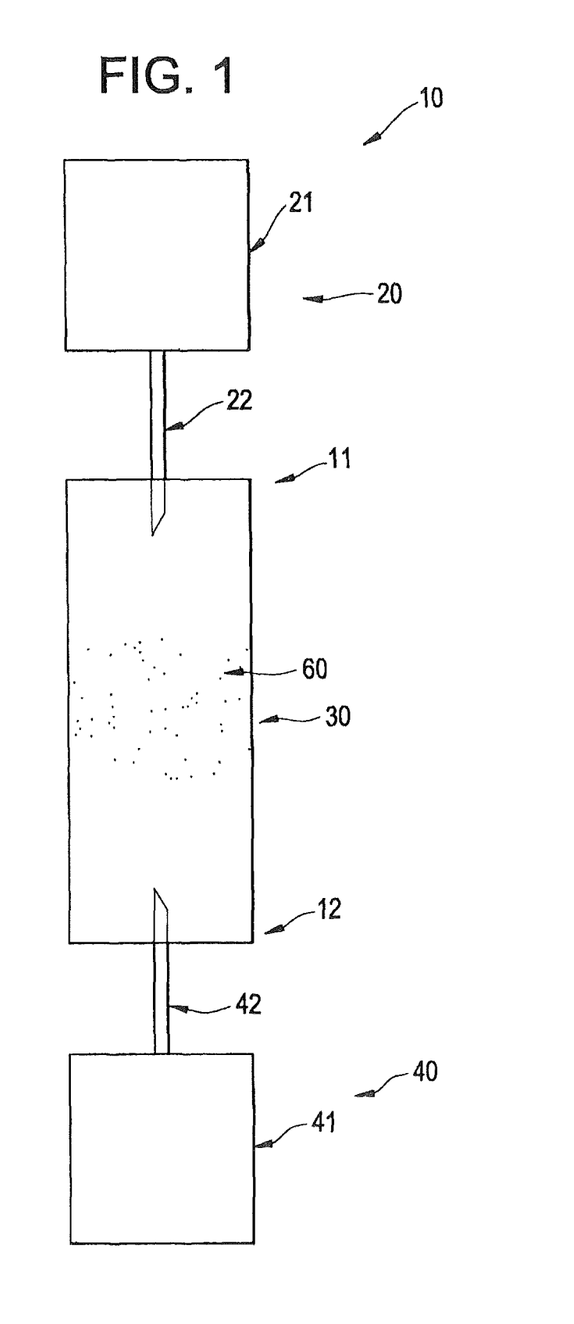
FIG. 1 is a section view of system for eluting a radioactive material according to an example embodiment of the present invention.

FIG. 1 illustrates an example of a system 10 for eluting a radioactive material 60. The system 10 includes an elution solution supply source 20, an elution column 30, and a collection system 40. The elution solution supply source 20 may include a reservoir 21 for storing elution solution and a hollow first needle 22 (an example of a first fluid communication path) configured to penetrate a first end 11 of the elution column 30 and to provide flow communication of the elution solution stored in the reservoir 21 to the elution column 30. The reservoir 21 may store, for example, saline solution. The collection system 40 may likewise include a hollow second needle 42 (an example of a second fluid communication path) configured to puncture a second end 12 of the elution column 30 and a storage chamber 41 for collecting the eluant from the elution column 30 via the second needle 42. The elution column 30 may resemble a vertically oriented cylinder which encloses the radioactive material 60.

In operation, elution column 30 is filled with a radioactive material 60. In order to remove desired ions from radioactive material 60, elution solution is made to pass from the elution solution supply source 20, through the first needle 22, through the radioactive material 60, through the second needle 42, and into the collection system 40. The above operations are driven by a vacuum applied to the system 10 from the collection system 40.

Figure 2:
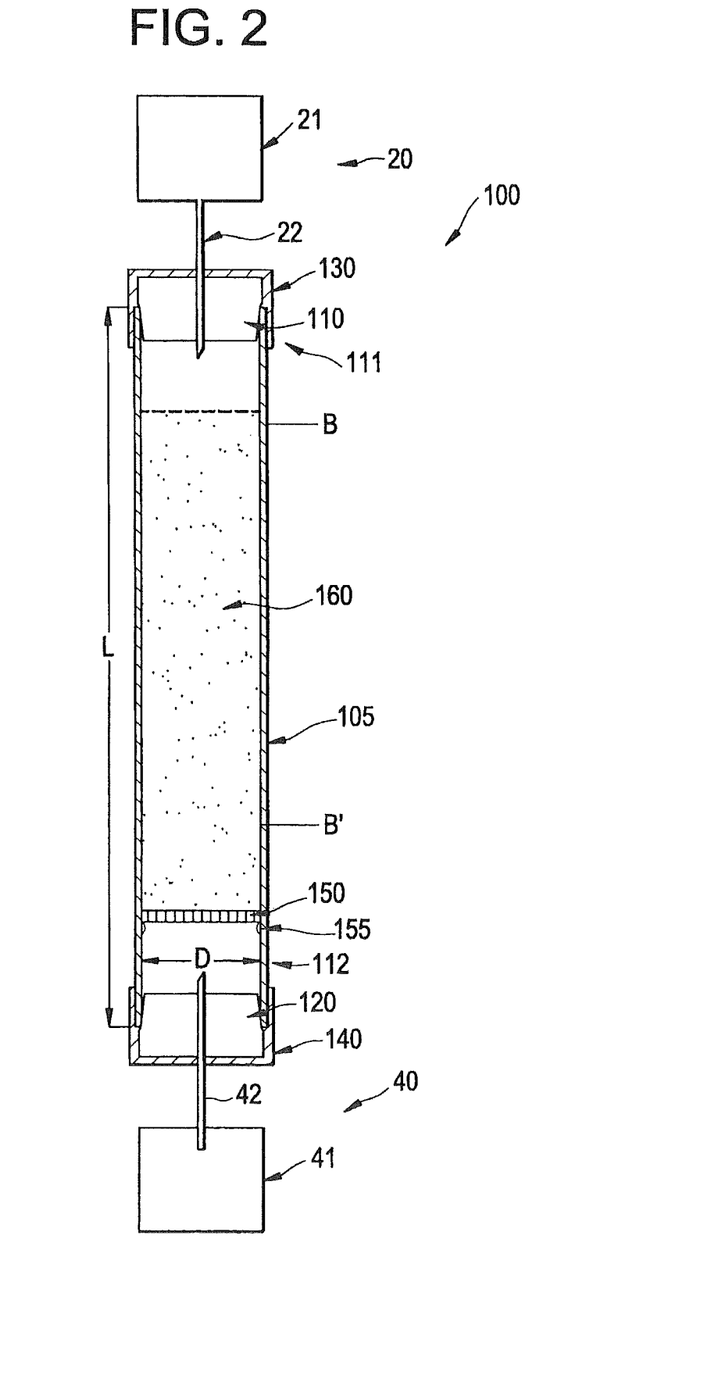
FIG. 2 is a section view of system for eluting a radioactive material according to an example embodiment of the present invention.

FIG. 2 illustrates an example embodiment of an elution system 100 that includes an elution solution supply source 20, a collection system 40, and an elution column 105 interposed therebetween. Like the system 10 illustrated in FIG. 1, the elution solution supply source 20 illustrated in FIG. 2 includes a first needle 22 which may be configured to penetrate a first end 111 of the elution column 105 and a reservoir 21 for storing elution solution. Similarly, the collection system 40 of system 100 also includes a second needle 42 configured to penetrate into a second end 112 of the elution column 105 and a storage chamber 41 for collecting eluant that has passed through the elution column 105.

In operation, the elution column 105 is filled with a radioactive material 160, for example, radioactive titanium molybdate. As shown in FIG. 2, the elution column 105 may resemble a hollow cylinder having an inner diameter D and a length L. A first end 111 of the elution column 105 may be sealed by a first sealing member 110 and a second end 112 of the elution column 105 may be sealed by a second sealing member 120. The first and second sealing members 110 and 120 may, for example, be rubber stoppers. As shown in FIG. 2, the first and second sealing members 110 and 120 may be formed as rubber stoppers that partially extend into the first and second ends 111 and 112 of the elution column 105. In addition to the first and second sealing members 110 and 120 sealing the first and second ends 111 and 112 of the elution column 105, end caps 130 and 140 may be provided over the first and second ends 111 and 112 of the elution column 105 to cover the first and second sealing members 110 and 120 and a portion of the elution column 105. The end caps 130 and 140 may function as an extra seal, may help protect the elution column 105, and may keep the stoppers in place. Though not illustrated in FIG. 2, an adhesive may be applied between inner walls of the end caps 130 and 140 and the outer walls of the elution column 105 to provide an extra seal.

As illustrated in FIG. 2, the elution column 105 encloses a radioactive material 160. In order to prevent the tip of the second needle 42 from being blocked by the radioactive material 160, a filter 150, for example, a glass fit, may be provided to support the radioactive material 160 in the column and act as a barrier to prevent the radioactive material 160 from contacting the second needle 42. In the event a glass frit is used as the filter 150, internal shoulders 155 may be provided in the elution column 105 to support the glass fit. The shoulders, for example, may be provided near the second end 112 of the elution column 105.

The elution column 105 may be relatively long and thin, medium, or relatively short and wide. For example, the column may have a length L of about 10⅝ inches and an internal diameter D of about ⅝ inches (an example of a relatively long and thin column). As another example, the column may have a length of about 5¼ inches and an internal diameter D of 1 inch (an example of a medium sized column). As another example, the column may have a length of about 4⅛ inches and an internal diameter D of 1 and 3/16 inches (an example of a short and wide column).

Each of the column geometries possess different properties which may affect the collection efficiency of the ions collected during the elution process. The long and thin column, for example, provides a longer flow path for the saline solution to pass through the radioactive material 160 thus increasing the opportunity for the saline solution to contact and remove ions from the radioactive material 160. The short and wide column offers a shorter flow path, however, because the flow path is shorter, the time for collecting the eluant is reduced. The Applicants studied the efficiencies of the long and thin column, the medium column, and the short and wide column. Initially, the Applicants believed the long and thin column would provide the greatest elution efficiency due to the longer flow path of the saline solution through the column, however, the Applicants discovered that of the three column sizes, the medium column obtained the best flow characteristics.

Figure 3:
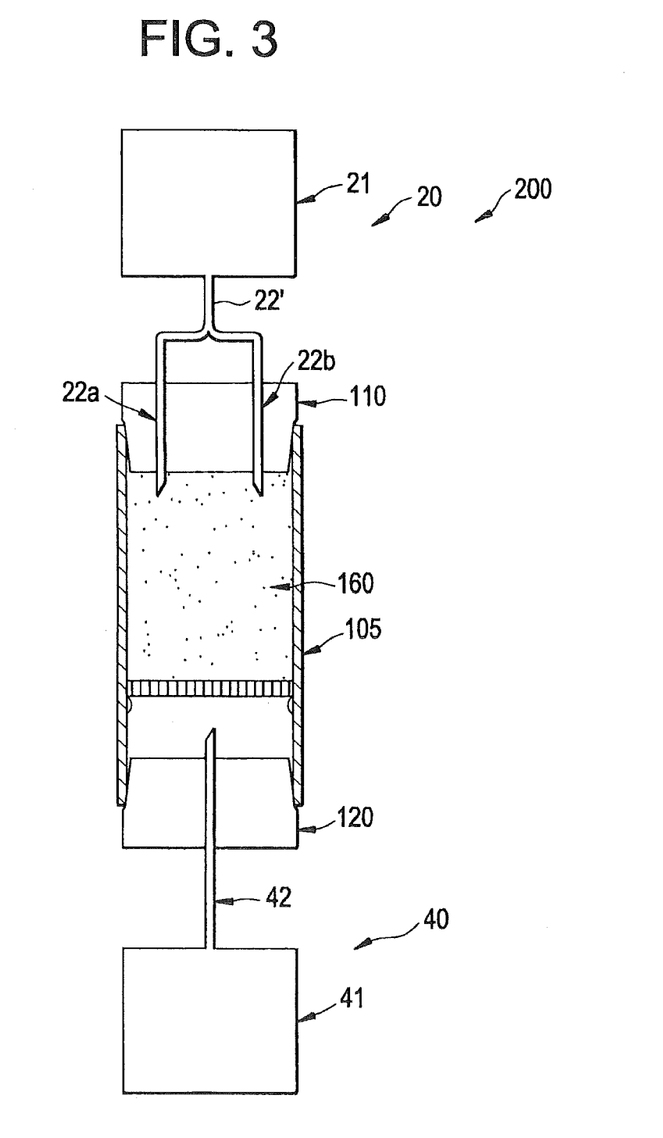
FIG. 3 is a section view of system for eluting a radioactive material according to an example embodiment of the present invention.

In FIG. 2, the elution solution supply source is illustrated as having only a single needle 22, however, example embodiments are not limited thereto. For example, as shown in FIG. 3, the elution solution supply source 20 may include a manifold type needle 22' which may include two sub-needles 22a and 22b which may penetrate a first sealing member 110 of the elution column 105. A manifold type needle 22' may increase the interaction of the elution solution with the radioactive material 160 since the elution solution is introduced to the radioactive material 160 at more than one location. Although FIG. 3 illustrates a system 200 using a manifold type needle 22' having two sub-needles 22a and 22b, example embodiments are not limited thereto. For example, the manifold type needle 22 may have more than two sub-needles. Other components illustrated in FIG. 3 may be identical to or similar to those described for system 100 illustrated in FIG. 2, therefore, for the sake of brevity, a discussion of the similar types of elements is omitted.

Figure 4:
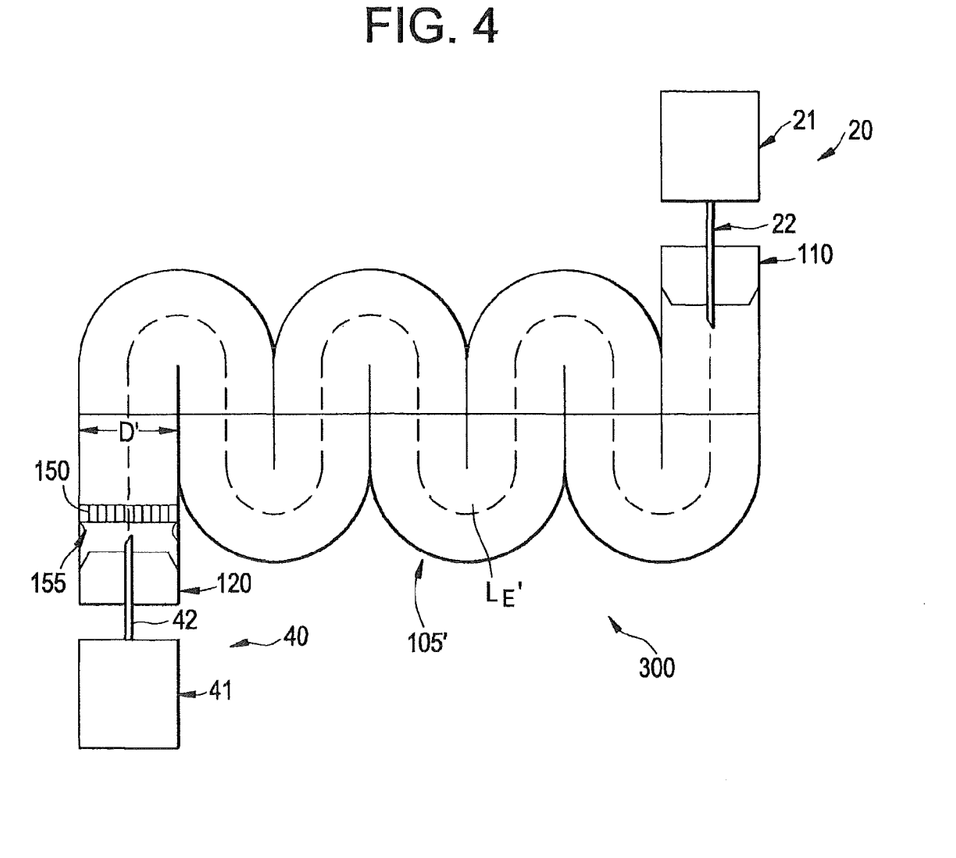
FIG. 4 is a section view of system for eluting a radioactive material according to an example embodiment of the present invention.
Figure 5:
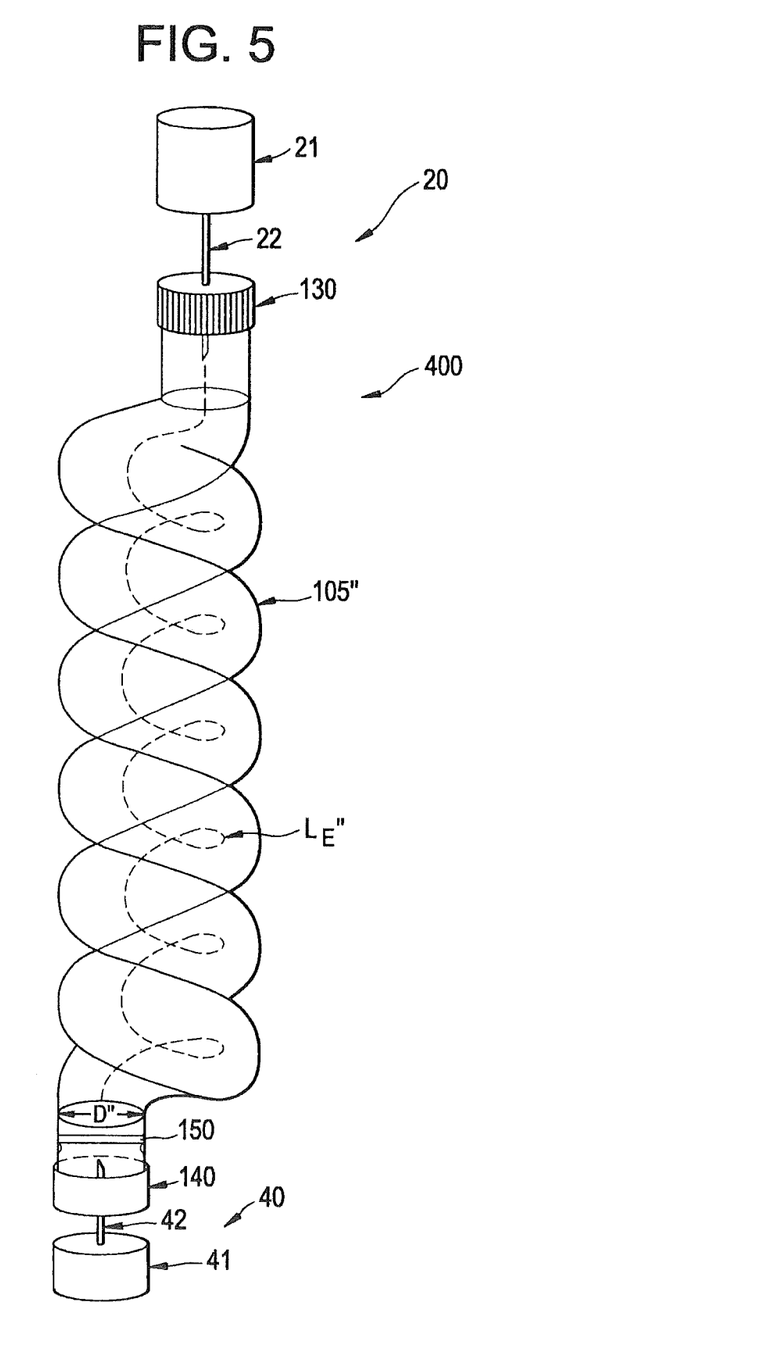
FIG. 5 is a section view of system for eluting a radioactive material according to an example embodiment of the present invention.

FIG. 2 illustrates an elution system 100 which includes a relatively straight cylindrical elution column 105, however, example embodiments are not limited thereto. For example, FIG. 4 illustrates a system 300 for eluting a radioactive material 160 which includes a "snake" shaped elution column 105'. For example, the elution column 105' illustrated in FIG. 4 includes a plurality of undulations. The effective length LE' of the "snake" shaped elution column 105', for example, may be about 10⅝ inches and the internal diameter D' of the "snake" shaped elution column 105' may be about ⅝ inches. In the alternative, rather than being "snake" shaped, the column may be "coil" shaped as illustrated in FIG. 5. In FIG. 5, a system 400 using a "coil" shaped elution column 105" is illustrated. The "coil" shaped elution column 105 may have an effective length LE" of about 10⅝ inches and an internal diameter D" of about ⅝ inches. Each of the "snake" and "coil" shaped elution columns 105' and 105" may provide for a compact elution column having a relatively long flow path through which elution solution may pass. The systems 300 and 400 illustrated in FIGS. 4 and 5 include components that are similar to those in system 100 illustrated in FIG. 2. Accordingly, a description of these components is omitted for the sake of brevity.

The inventors have determined the efficiency of the elution systems 300 and 400 may be increased relative to the system disclosed in FIG. 2 since the "snake" and "coil" shaped elution columns 105' and 105" change the flow direction of the eluant passing through the elution columns 105' and 105". Thus, the flow of the eluant flowing through the "snake" and "coil" shaped elution columns 105' and 105" is directed in a relatively turbulent manner, thus allowing for greater interaction between the elution solution and the radioactive material 160.

FIG. 2 illustrates an elution system 100 which includes a relatively straight elution column 105. As previously explained, the elution column 105 may be filled with a radioactive material 160, for example titanium molybdate, through which an elution solution, for example, saline solution, may pass under the influence of a vacuum applied by the collection system 40. The flow path of the elution solution through the titanium molybdate may be substantially vertical. Accordingly, some of the radioactive material 160 may not be touched by the elution solution. The inventors have determined the efficiency of the elution system may be increased if the elution solution were directed in a turbulent manner, thus allowing for greater interaction between the elution solution and the radioactive material 160.

Figure 6:
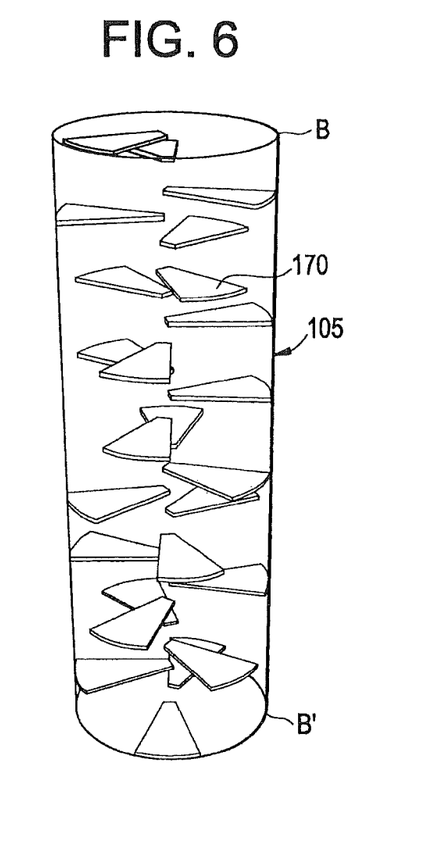
FIG. 6 is a section view of a portion of an elution column which includes flow trippers according to an example embodiment of the present invention.
Figure 7:
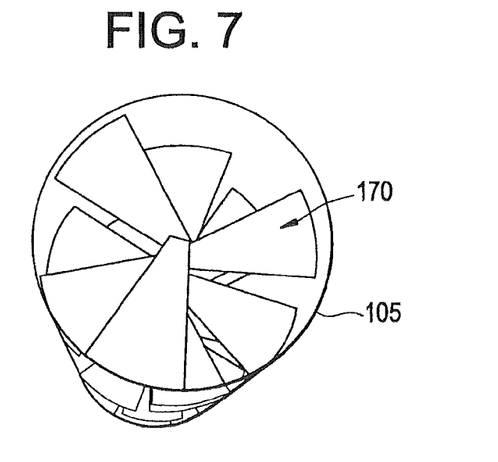
FIG. 7 is a view of a portion of an elution column which includes flow trippers according to an example embodiment of the present invention.

FIGS. 6 and 7 illustrate the addition of flow trippers 170 to the elution column 105 illustrated in FIG. 2. The flow trippers 170 resemble a plurality of wedge like elements which protrude from the inner wall of the elution column 105 towards the center of the elution column 105. The flow trippers 170 may be arranged in a regular pattern, for example, in a helical pattern, or may be arranged randomly. The flow trippers 170 may be provided in a portion of the elution column 105 which is filled with the radioactive material 160, for example, in the region marked B-B' of FIG. 2. Although flow trippers 170 are not required in order to effectively elute the radioactive material 160, the addition of the flow trippers 170 may increase the efficiency of the elution process since the flow path of the eluant through the radioactive material 160 is periodically changed. This change in flow path may allow for the elution solution to contact portions of the radioactive material 160 which may not normally be contacted by the elution solution in the event the flow trippers 170 were not provided. The flow trippers 170 may be made from a relatively nonreactive material, for example, glass.

As shown in FIG. 6, the flow trippers 170 may resemble wedge shaped elements, however, example embodiments are not limited thereto. For example, the flow trippers 170 may be rectangular shaped. Also, FIG. 6 illustrates the flow trippers 170 as being substantially horizontal, however, example embodiments are not limited thereto. For example, the flow trippers 170 may be inclined from the horizontal direction. Additionally, FIG. 6 illustrates the flow trippers 170 being relatively flat, however, example embodiments are not limited thereto. For example, the flow trippers 170 may have a curved or inclined surface.

Figure 8:
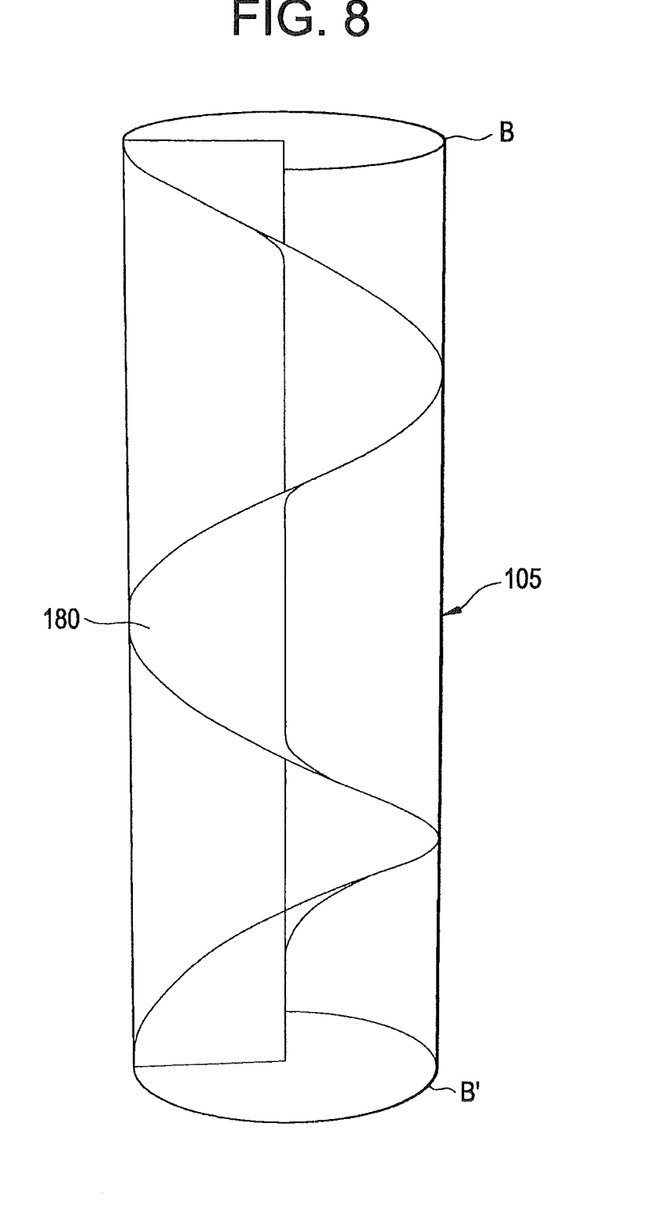
FIG. 8 is a view of a portion of an elution column which includes a spiraling platform according to an example embodiment of the present invention.
Figure 9:
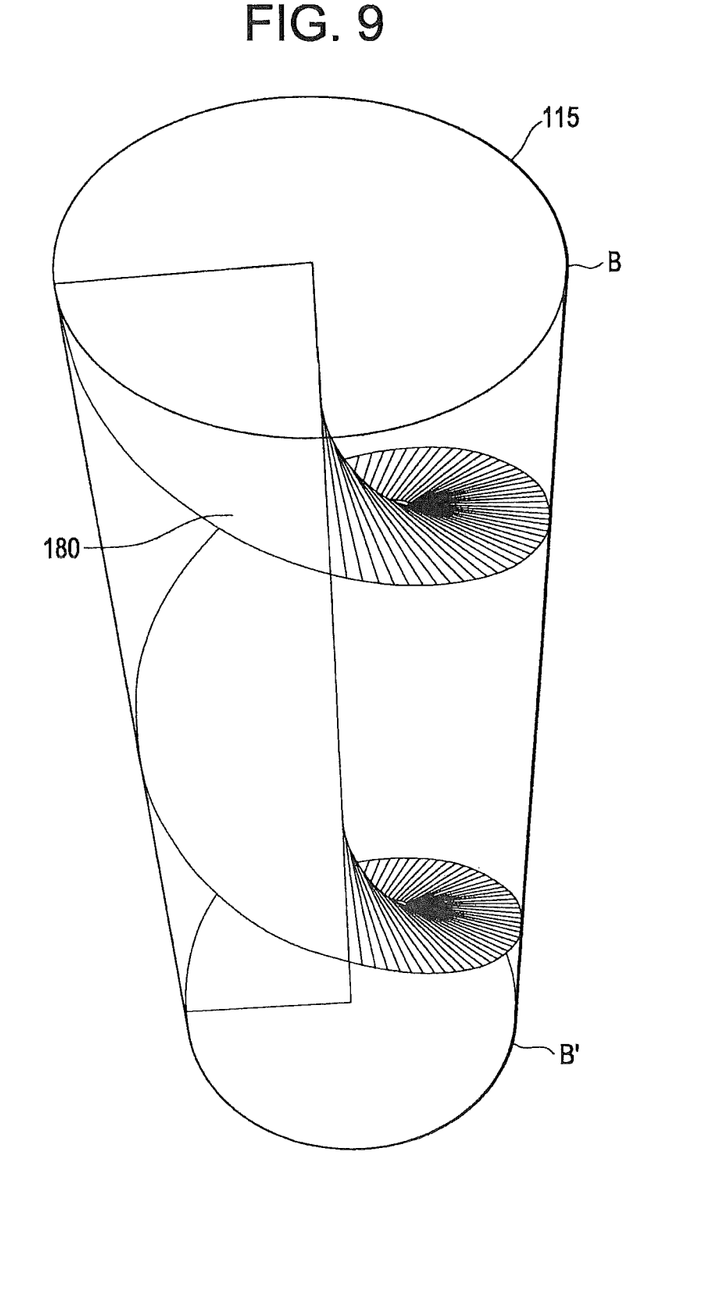
FIG. 9 is a view of a portion of an elution column which includes a spiraling platform according to an example embodiment of the present invention.

Rather than providing flow trippers 170 in region B-B' of the elution column 105 illustrated in FIG. 2, the elution column 105 may include a spiraling platform 180 as illustrated in FIGS. 8-9. As shown in FIGS. 8-9, the spiraling platform 180 may force the eluant to travel in a spiraling flow path rather than a vertical flow path thus increasing the flow path of the eluant. The spiraling platform 180 may either include a smooth surface, as shown in FIG. 8, or a stepped surface, as shown in the flow trippers in FIG. 6. Because the flow path of the eluant is increased, the interaction between the elution solution and the radioactive material 160 is increased which may increase the elution efficiency. The spiraling platform 180 may be made from a relatively nonreactive material, for example, glass.

Figure 10:
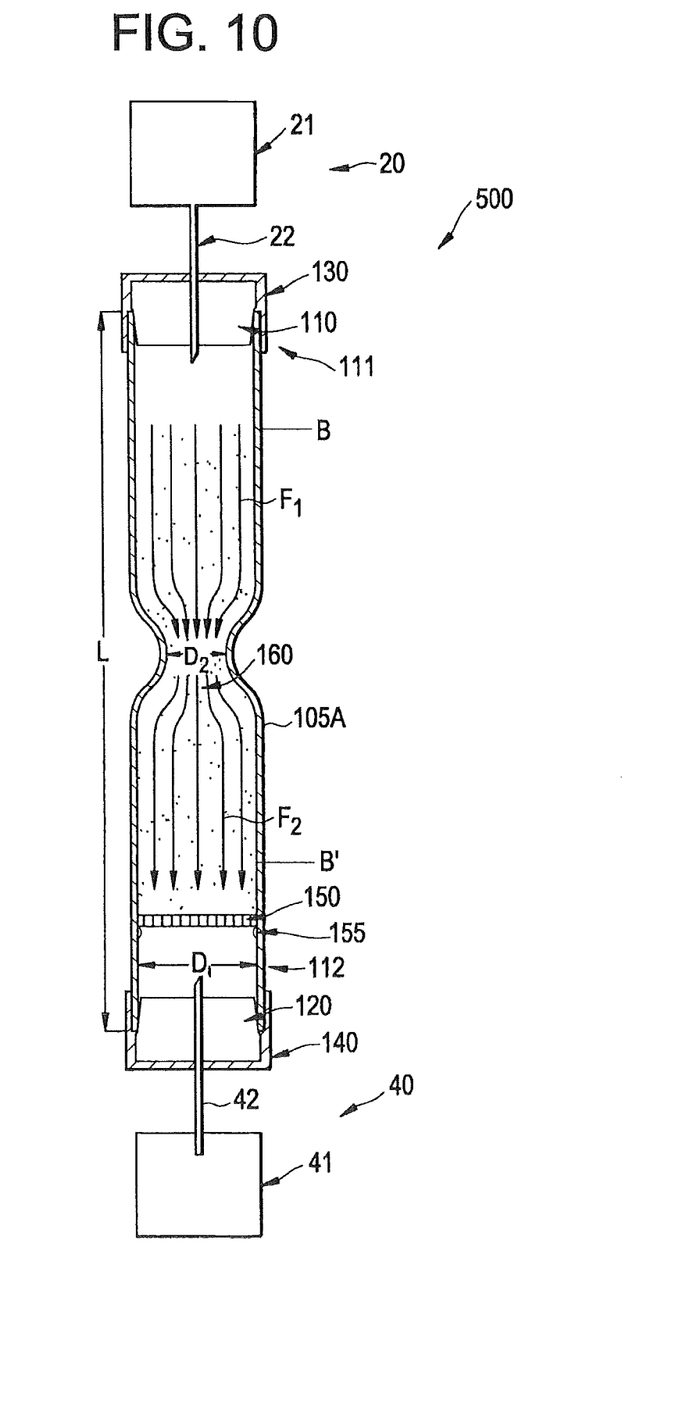
FIG. 10 is a section view of system for eluting a radioactive material according to an example embodiment of the present invention.

As described above, example embodiments provide various configurations of elution columns. Each of the aforementioned elution columns are configured so that the internal diameters of each column are relatively constant, however, example embodiments are not limited thereto. For example, FIG. 10 illustrates a system 500 including an example elution column 105A which resembles an hourglass having a diameter D1 at the ends of the column and a smaller diameter D2 near the middle of the column. Because the column 105A is hourglass shaped, the flow path of the elution solution through the hourglass changes near the middle of the center of the column. For example, the flow path F1 of the elution solution above the middle of the elution column converges near the middle of the column. However, due to the narrowing of the elution column 105A, the flow path of the elution solution is changed at the middle of the elution column 105A and transformed into flow path F2 emerging out of the middle portion of the column. The hourglass shaped elution column 105A may increase elution efficiency for at least two reasons. First, the flow path of the eluant is longer allowing for greater interaction between the radioactive material 160 and the elution solution. Second, the flow path of the elution solution passing through the hourglass shaped elution column 105A is more turbulent than the flow of the elution solution passing through the cylindrical shaped elution column 105, thus, increasing the interaction between the elution solution and the radioactive material 160. The system 500 may include components which are similar to components used with system 100 illustrated in FIG. 2. Accordingly, a discussion of these elements is omitted for the sake of brevity.

Figure 11:
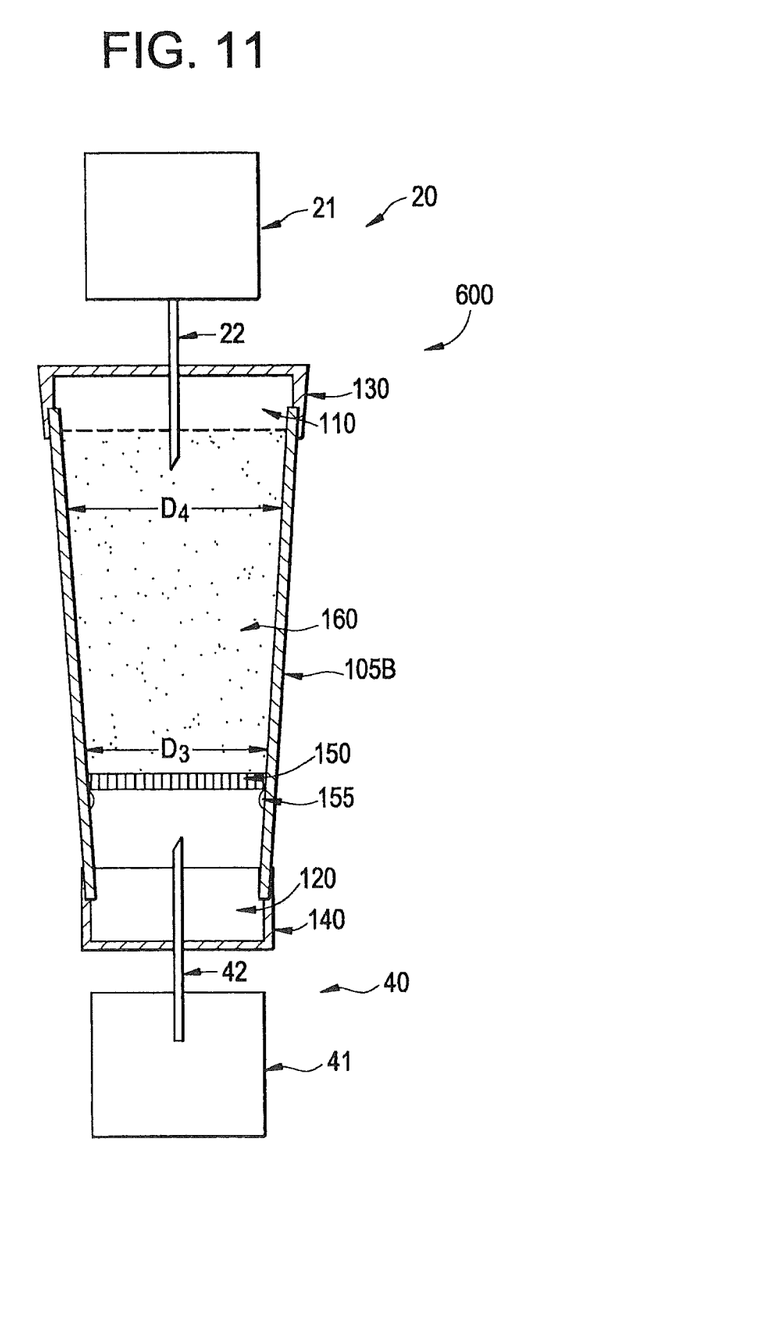
FIG. 11 is a section view of system for eluting a radioactive material according to an example embodiment of the present invention.

FIG. 11 illustrates another example of an elution system 600. The system 600 illustrated in FIG. 11 is similar the elution system 100 illustrated in FIG. 2 and therefore a detailed discussion thereof is omitted for the sake of brevity. The primary difference between the system 100 illustrated in FIG. 2 and the system 600 illustrated in FIG. 6 involves the shape of the column 105B. In the system 100 illustrated in FIG. 2 the column 105 is cylindrically shaped with a constant inner diameter D whereas the column of system 600 is funnel shaped having a diameter D4 at the top of the elution column 105B larger than the diameter D3 near the bottom of the elution column 105B. Accordingly, the flow path of the elution solution passing through the elution column 105B, while being substantially vertical, may be inclined allowing for a longer flow path of the elution solution through the elution column 105B. Accordingly, the interaction between the elution solution in system 600 and the radioactive material 160 may be greater than the interaction of the elution solution in system 100 and the radioactive material 160 of system 100. Accordingly, the efficiency of the system illustrated in FIG. 6 may be higher than the efficiency of the system 100 illustrated in FIG. 2 having the cylindrical elution column 105.

Figure 12:
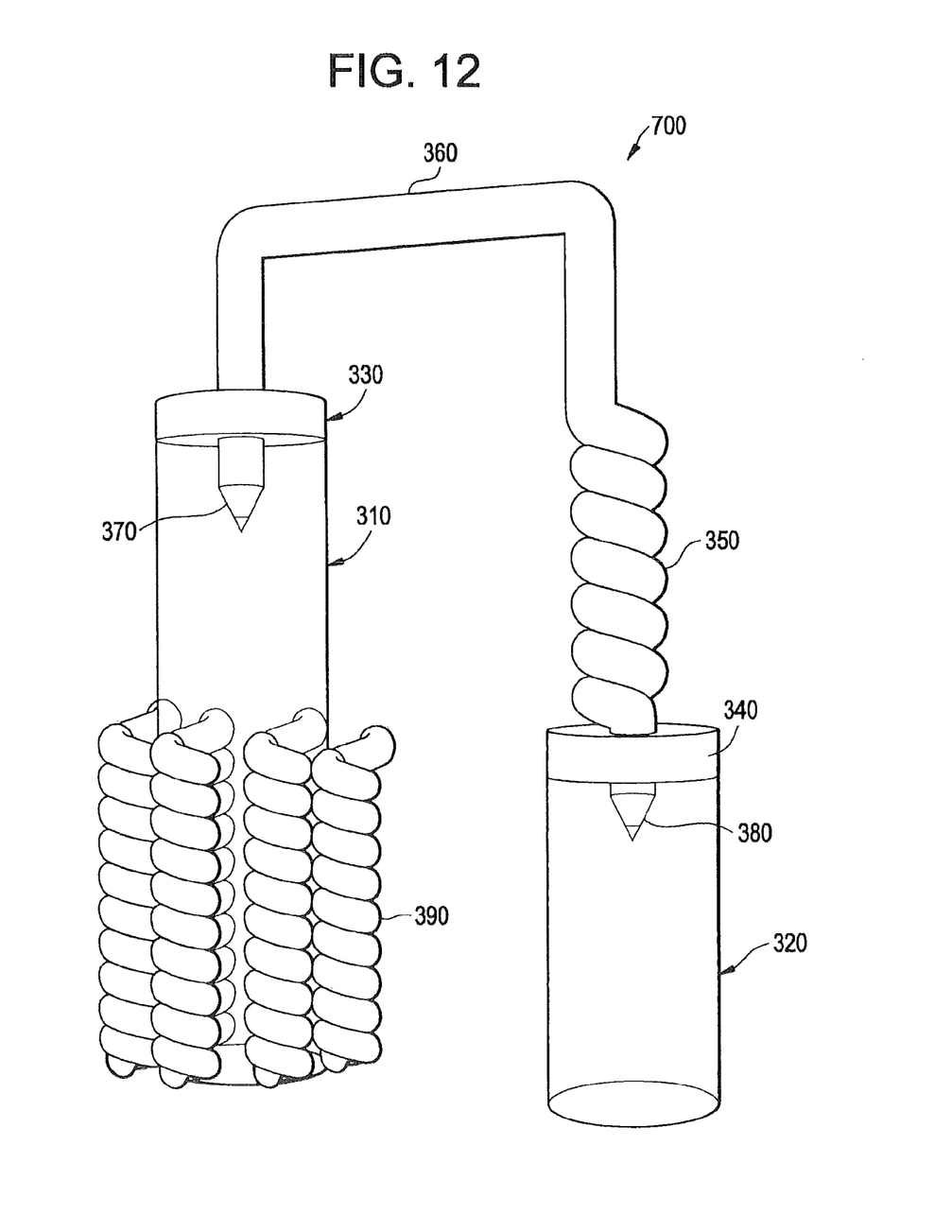
FIG. 12 is a view of system for eluting a radioactive material according to an example embodiment of the present invention.

FIG. 12 represents a system 700 for collecting ions from a radioactive material. The system 700 may include a first cylinder 310 sealed by a first end cap 330, a second cylinder 320 sealed by a second end cap 340, a tube 360 connecting the first cylinder 310 to the second cylinder 320, and a heater 390 configured to heat the first cylinder 310. As shown in FIG. 12, the tube 360 may include a first end portion 370 penetrating through the first end cap 330 and into the first cylinder 310 and a second end portion 380 penetrating through the second end cap 340 and into the second cylinder 320. The tube 360 may also include a coiled portion 350 to facilitate a cooling of a vapor that may be in the tube 360. The tube 360 may provide fluid communication between the first and second cylinders 310 and 320.

In this example embodiment, an elution solution, for example, saline solution, may be mixed with a radioactive material, for example, titanium molybdate and stored in the first cylinder 310. The heater 390 surrounding the first cylinder 310 may generate heat to boil the elution solution with the radioactive material mixed therein. The gaseous elution solution carries ions, for example, technetium-99m ions, from the elution solution-radioactive material-mixture and into the tube 360 via the first end portion 370 of the tube 360. The gaseous elution solution with the ions then travels to the coiled portion 350 of the tube 360 where the gaseous elution solution condenses out and drips into the second cylinder 320 via the second end portion 380. Accordingly, ions, for example technetium-99m, may be collected via the condensation apparatus illustrated in FIG. 12. As one skilled in the art would appreciate, the first and second cylinders 310 and 320 as well as the tube 360 should be made from materials that are relatively nonreactive, for example, glass. However, one skilled in the art may recognize a host of materials that may be suitable for the elution system 700 illustrated in FIG. 12

Figure 13:
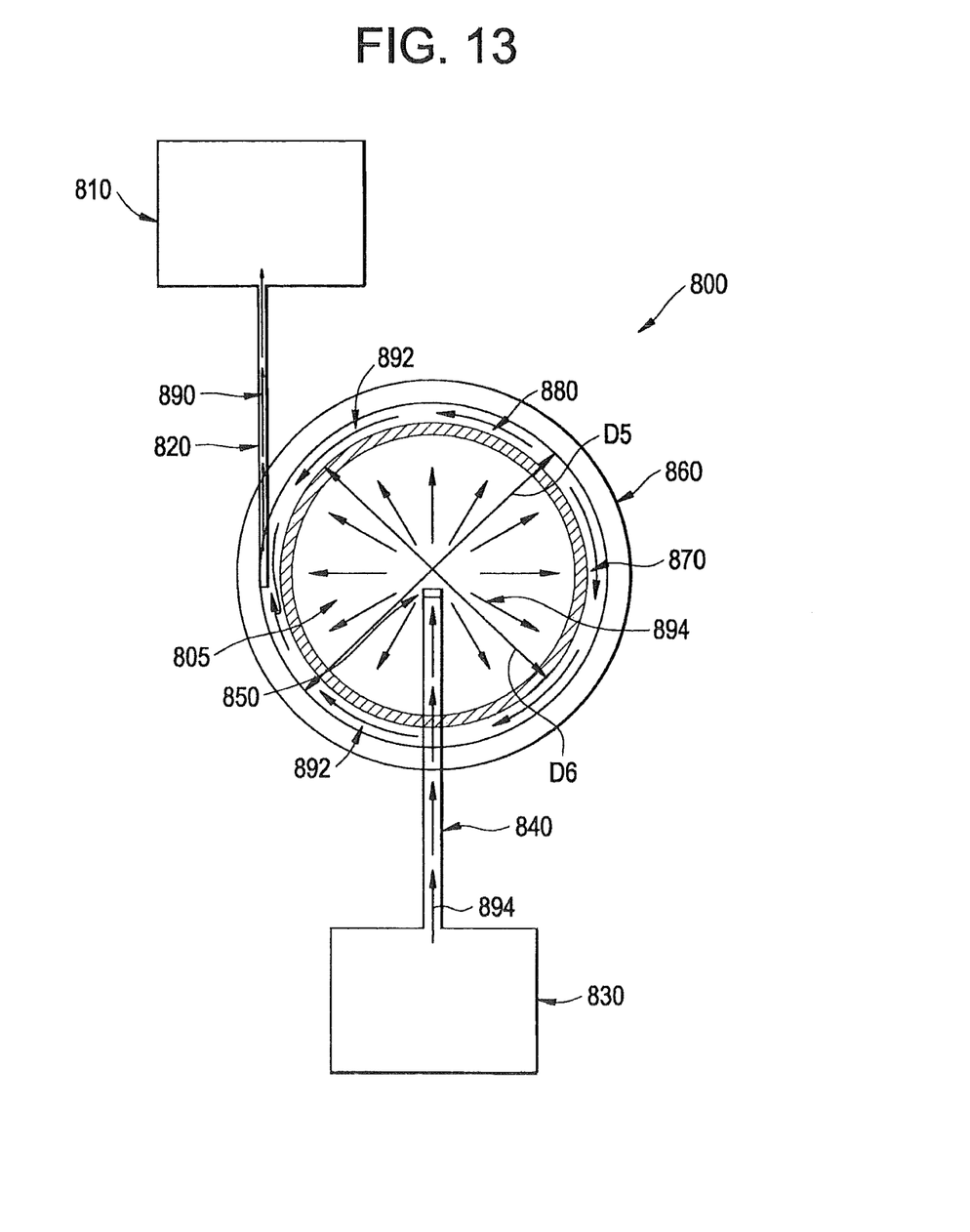
FIG. 13 is a section view of system for eluting a radioactive material according to an example embodiment of the present invention.

Referring to FIG. 13, a cross-section of a system 800 for eluting a radioactive material 805 may utilize a spherical shaped capsule 860. As shown in FIG. 13, the example system 800 for eluting a radioactive material 805 may include an elution solution supply source 830, a spherical shaped capsule 860, and a collection system 810. A tube 840 may connect the elution solution supply source 830 to the spherical shaped capsule 860 to introduce elution solution, for example, saline solution, into the spherical shaped capsule 860. Another tube 820 may connect the collection system 810 to the spherical shaped capsule 860 to collect the eluant that has passed through the radioactive material 805. The spherical shaped capsule 860 may enclose a membrane 870 filled with a radioactive material 805, for example, radioactive titanium molybdate. The membrane 870, for example, may be made from saline permeable substance, for example, a cellulosic material or polymers. The membrane 870 filled with the radioactive material 805 may be punctured by the tube 840 connected to the elution solution supply source 830. In order to prevent the radioactive material 805 from entering the elution solution supply source 830, a filter 850, for example, a glass fit, may be attached to an end of the tube 840.

The spherical shaped capsule 860 may have an inner diameter D5 of about 3 inches and the membrane 870 may have an outer diameter D6 of about 2.75 inches. Accordingly, in the example system 800 illustrated in FIG. 13 a gap between the inner surface of the spherical shaped capsule 860 and the membrane 870 may be about 0.125 inches.

In operation, elution solution enters the spherical shaped capsule 860 via the tube 840 connected to the elution solution supply source 830. A flow pattern of the elution solution leaving the elution solution supply source 830 is illustrated as 894. Upon entering the center of the membrane 870, the elution solution flows through the radioactive material 805, and may pass through the membrane 870 and into a space 880 between the spherical shaped capsule 860 and the membrane 870. The flow pattern of the elution solution in space 880 is illustrated by symbol 892 as illustrated in FIG. 13. Because the collection system 810 applies a vacuum to the outside of the membrane 870, the elution solution may be drawn from the space 880 and into the collection system 810 via the tube 820. The flowpath of the eluant passing through the tube 820 is illustrated by symbol 890. The flow pattern of the elution solution inside the membrane 870 is illustrated in FIG. 13 by symbol 894. Accordingly, the elution solution passes through the radioactive material 805 from various angles.

As one skilled in the art would readily appreciate, tubes 820 and 840 as well as the spherical shaped capsule 860 should be made from a relatively nonreactive material, for example, glass or a polymer.

While example embodiments have been particularly shown and described with reference to example embodiments thereof, it will be understood by those of ordinary skill in the art that various changes in form and details may be made therein without departing from the spirit and scope of the following claims. It will also be understood that while a saline solution has been used as an example of elution solution for used with the example systems, example embodiments are not limited to using a saline solution as elution solution. In addition, while radioactive titanium molybdate has been used to exemplify a radioactive material that may be used with the aforementioned elution systems, it will be understood that the elution system may be used with other radioactive materials. Additionally, while technetium-99m has been used to exemplify an ion that may be eluted from a radioactive material, example embodiments are not limited thereto.

What is claimed:
1. A system for eluting a radioactive material, comprising:
an elution column, at least a portion of the elution column enclosing and being substantially filled with the radioactive material;
a first sealing member sealing a first end of the elution column;
a second sealing member sealing a second end of the elution column;

only a single elution supply source for the system, the single elution supply source being connected to the first end of the elution column via a first fluid communication path;

a collection system connected to the second end of the elution column via a second fluid communication path, the first and second fluid communication paths being in continuous fluid communication with the elution column during the eluting of the radioactive material, the first and second fluid communication paths being the only fluid communication paths fluidly connected to the elution column; and a filter on an eluant discharge end of the portion of the elution column enclosing the radioactive material, the filter being configured to support the radioactive material and prevent the radioactive material from contacting the second fluid communication path, wherein the radioactive material enclosed by the elution column is titanium Molybdate, the elution supply source introduces saline solution into the system in order to allow the saline solution to gravity drain through the elution column, and the collection system collects technetium-99m ions, wherein a length of the elution column is between about 4⅛ inches and 10⅝ inches and an inner diameter of the elution column is between about ⅝ inches and 1 3/16 inches.

2. The system of claim 1, wherein a length of the column is about 10⅝ inches and an inner diameter of the elution column is about ⅝ inches.

3. The system of claim 1, wherein a length of the column is about 5¼ inches and an inner diameter of the elution column is about 1 inch.

4. The system of claim 1, wherein a length of the column is about 4⅛ inches and an inner diameter of the elution column is about 1 and 3/16 inches.

5. The system of claim 1, wherein the filter is a glass frit and the glass frit is supported by internal shoulders of the elution column.

6. The system of claim 1, wherein the first fluid communication path is a manifold type needle including at least two subneedles.

7. The system of claim 1, wherein the portion of the elution column enclosing the radioactive material includes a plurality of undulations.

8. The system of claim 1, wherein the portion of the elution column enclosing the radioactive material is coil-shaped.

9. The system of claim 1, further comprising:
a plurality of flow trippers attached to an inside wall of the portion of the elution column enclosing the radioactive material.

10. The system of claim 9, wherein each of the flow trippers have one end attached to an inside wall of the elution column and another end extending towards a center of the elution column.

11. The system of claim 9, wherein the flow trippers have a wedge shape.

12. The system of claim 9, wherein the flow trippers have an upper curved surface.

13. The system of claim 9, wherein the flow trippers are regularly arranged in a spiral pattern along a length of the column.

14. The system of claim 1, further comprising:
a spiraling platform attached to an inner wall of the portion of the elution column enclosing the radioactive material.

15. The system of claim 1, wherein the portion of the elution column enclosing the radioactive material has an hourglass shape.

16. The system of claim 1, wherein the portion of the elution column enclosing the radioactive material has a funnel shape.

17. The system of claim 1, wherein the system does not require any adsorbent material on a downstream side of the filter on the eluant discharge end of the portion of the elution column enclosing the radioactive material.

18. The system of claim 1, wherein the system does not require adsorbent packing material.

19. A system for eluting a radioactive material, comprising:
an elution column, at least a portion of the elution column enclosing and being substantially filled with the radioactive material;

a first sealing member sealing a first end of the elution column;

a second sealing member sealing a second end of the elution column;

an elution supply source for the system, the single elution supply source being connected to the first end of the elution column via a first fluid communication path, the system not including more than one elution supply source;

a collection system connected to the second end of the elution column via a second fluid communication path, the first and second fluid communication paths being in continuous fluid communication with the elution column during the eluting of the radioactive material, the first and second communication paths being the only fluid communication paths fluidly connected to the elution column; and a filter on an eluant discharge end of the portion of the elution column enclosing the radioactive material, the filter being configured to support the radioactive material and prevent the radioactive material from contacting the second fluid communication path, wherein the radioactive material enclosed by the elution column is titanium Molybdate, the elution supply source introduces saline solution into the system in order to allow the saline solution to gravity drain through the elution column, and the collection system collects technetium-99m ions, wherein a length of the elution column is between about 4⅛ inches and 10⅝ inches and an inner diameter of the elution column is between about ⅝ inches and 1 3/16 inches.

20. The system of claim 19, wherein the system does not require any adsorbent material on a downstream side of the filter on the eluant discharge end of the portion of the elution column enclosing the radioactive material.

21. The system of claim 19, wherein the system does not require adsorbent packing material.

22. The system of claim 19, wherein,
the first sealing member is part of the first end of the elution column,
the second sealing member is part of the second end of the elution column,
the elution column is a uniform diameter from the first end of the elution column to the second end of the elution column.

23. A system for eluting a radioactive material, comprising:
an elution column with a first end and a second end, at least a portion of the elution column enclosing and being substantially filled with the radioactive material;

a first sealing member included in the first end of the elution column, the first sealing member being configured to seal the first end of the elution column;

a second sealing member included in the second end of the elution column, the second sealing member being configured to seal the second end of the elution column;

only a single elution supply source for the system, the single elution supply source being connected to the first end of the elution column via a first fluid communication path;

a collection system connected to the second end of the elution column via a second fluid communication path, the first and second fluid communication paths being in continuous fluid communication with the elution column during the eluting of the radioactive material, the first and second fluid communication paths being the only fluid communication paths fluidly connected to the elution column; and a filter on an eluant discharge end of the portion of the elution column enclosing the radioactive material, the filter being configured to support the radioactive material and prevent the radioactive material from contacting the second fluid communication path, wherein the elution column is a uniform diameter from the first end of the elution column to the second end of the elution column.

24. The system of claim 23, wherein, the system is configured to allow an elution solution to gravity drain through the elution column, a length of the elution column is between about $4\frac{1}{8}$ inches and $10\frac{5}{8}$ inches and an inner diameter of the elution column is between about $\frac{5}{8}$ inches and $1\frac{3}{16}$ inches.

* * * * *